United States Patent
Chamanzar et al.

(10) Patent No.: US 11,612,768 B2
(45) Date of Patent: Mar. 28, 2023

(54) IN-MEDIUM SCULPTED TUNABLE GRADED INDEX LENSES

(71) Applicant: Carnegie Mellon University, Pittsburgh, PA (US)

(72) Inventors: Maysamreza Chamanzar, Pittsburgh, PA (US); Matteo Giuseppe Scopelliti, Pittsburgh, PA (US); Yasin Karimi Chalmiani, Pittsburgh, PA (US)

(73) Assignee: CARNEGIE MELLON UNIVERSITY, Pittsburgh, PA (US)

( * ) Notice: Subject to any disclaimer, the term of this patent is extended or adjusted under 35 U.S.C. 154(b) by 367 days.

(21) Appl. No.: 16/522,331

(22) Filed: Jul. 25, 2019

(65) Prior Publication Data

US 2020/0030638 A1   Jan. 30, 2020

Related U.S. Application Data

(60) Provisional application No. 62/764,295, filed on Jul. 26, 2018.

(51) Int. Cl.
| | |
|---|---|
| *A61N 7/00* | (2006.01) |
| *A61B 5/00* | (2006.01) |
| *G02F 1/125* | (2006.01) |

(52) U.S. Cl.
CPC .............. *A61N 7/00* (2013.01); *A61B 5/0077* (2013.01); *G02F 1/125* (2013.01); *A61N 2007/006* (2013.01); *A61N 2007/0073* (2013.01)

(58) Field of Classification Search
CPC .............. A61N 7/00; A61N 2007/0073; A61N 2007/006; G02F 1/125; A61B 5/0077
See application file for complete search history.

(56) References Cited

U.S. PATENT DOCUMENTS

| | | | |
|---|---|---|---|
| 2013/0229665 A1* | 9/2013 | Nomura | G01B 11/24 356/601 |
| 2018/0010961 A1* | 1/2018 | Masumura | A61B 5/0095 |

* cited by examiner

*Primary Examiner* — Hien N Nguyen
(74) *Attorney, Agent, or Firm* — KDB Firm PLLC (57) ABSTRACT

Disclosed herein is a novel technique that employs non-invasive ultrasound for spatiotemporal modulation of the refractive index in a medium to define and control the trajectory of light within the medium itself, thereby creating a virtual sculpted lens. By varying the amplitude of ultrasonic waves in the medium, the numerical aperture (NA) value of the virtual sculpted lens can be changed. The location of the focus of the virtual sculpted lens can be precisely scanned within a scattering tissue.

24 Claims, 7 Drawing Sheets
(7 of 7 Drawing Sheet(s) Filed in Color)

IN-MEDIUM SCULPTED TUNABLE GRADED INDEX LENSES

RELATED APPLICATIONS

This application claims the benefit of U.S. Provisional Patent Application No. 62/764,295, filed Jul. 26, 2018, the contents of which are incorporated herein in their entirety.

BACKGROUND OF THE INVENTION

Imaging and light delivery through biological tissue has always been one of the most important challenges for research and applications in the medical field. The ability of light to penetrate and interact with tissue via optical scattering and absorption is crucial in diagnostics and therapies, such as photodynamic therapy (PDT), and would be an enabling factor for new applications in brain study, for example, the use of optogenetics.

While both absorption and scattering play important roles in preventing the deep delivery of light in tissue, scattering is the main reason for the opacity of the tissue in the visible and near infrared band. When scattering particles are comparable in size to the light wavelength, Mie scattering dominates, and when the size of such particles is smaller than the wavelength of the incident beam, Rayleigh scattering is predominant. Because biological tissue is a heterogeneous mix of particles sized comparably to the wavelength of visible light (such as nuclei and organelles) or smaller (macromolecular aggregates and membranes), both Mie and Rayleigh scattering affect the propagation of light.

Another aspect to consider is the difference between the components of the cell, the refractive index of which is strongly dependent on the amount of proteins, nucleic acids and lipids present. For example, the refractive index of the membrane is $n_m=1.5\text{-}1.6$, sensibly larger than the cytoplasm refractive index $n_c=1.35$. The refractive index mismatch further increases the scattering effect.

As a result, when a collimated beam of light enters a tissue sample, it will be attenuated by absorption and, to a greater extent, expanded by the scattering. Intensity of light, defined as power over area $$\left(\frac{mW}{mm^2}\right),$$

will increasingly drop with the number of scattering events that the beam undergoes along its paths (increasing with the depth of the tissue), and consequently, the energy delivered to the tissue will be decreased. Increasing the power is not a valid solution to compensate for the loss of intensity, because increasing the energy over a large area (poor spatial resolution) will cause stronger background noise in imaging applications, such as fluorescent microscopy, as well as stimulation of unwanted targets in optogenetic and therapeutic applications.

Traditional optical methods have limitations in imaging and stimulation of biological tissue. To address the poor penetration of light and low spatial resolution, current methods require implantable optical elements, such as waveguides, optical fibers and implantable graded-index media (GRIN) lenses to physically guide the beam of light through the tissue and deliver it to the area of interest with the intended intensity and resolution. For example, small implantable GRIN lenses, with a diameter on the order of millimeters, are the enabling technology for miniaturized endoscopes, which work by relaying the image plane inside the tissue to a powerful objective lens placed outside. A typical application for this system is IP calcium imaging in rodents for optogenetic experiments, where the mouse is awake and free to roam.

While traditional methods can deliver light at great depth inside the tissue, they are invasive, and the light output depends on their physical design (such as geometry and materials), so it is fixed to a single area. As a result, once the optical element is implanted, it is not possible to change the focal plane and image a 3D volume in the tissue without physically moving the element itself, wand triggering the consequential inflammatory response. The same limitation applies to optical stimulation, where it would be extremely beneficial to be able to move the focal point in the tissue to precisely stimulate targets at different depths.

A solution to these problems could be a virtual and tunable relay lens, to direct the light into the tissue non-invasively (e.g. ultrasonic waves). The capability of acoustic waves to modulate and shape a beam of light is well known, and is the basis of affirmed technologies, such as acousto-optic modulators and, more recently, TAG optics. However, these technologies work by modulating a specific material (crystal and oil for the previous two examples, respectively), and their dimension and structure snake them un-implantable. Additionally, the shaped output beams are affected by the typical limitations of external optics when used to deliver light or image through a scattering tissue, where the ballistic photon region is limited to 1 MFP.

SUMMARY OF THE INVENTION

Figure 1:
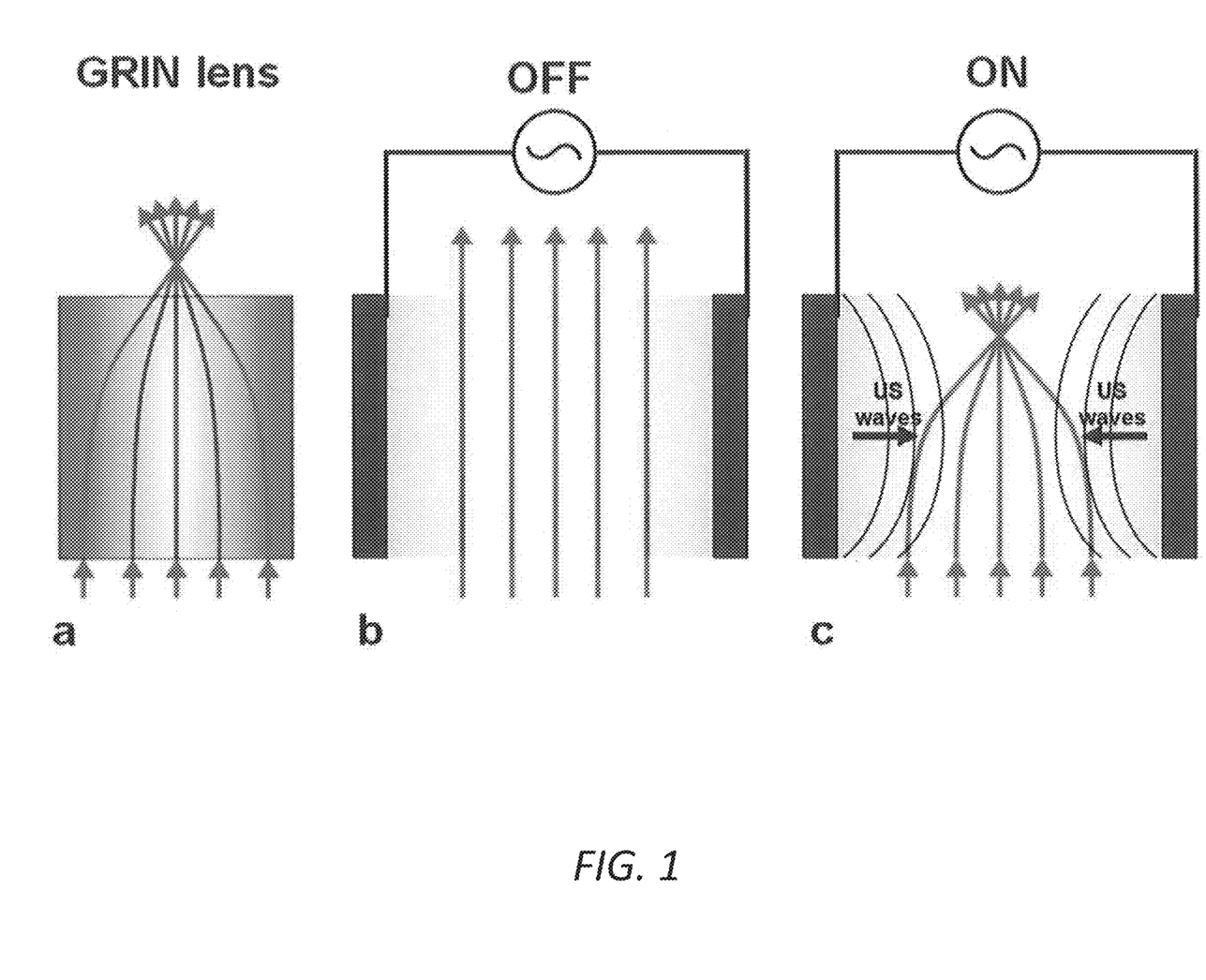
FIG. 1, View (a) schematically shows a prior-art GRIN lens. View (b) shows a collimated beam having an unvaried path, and View (c) shows a collimated beam having a path altered by the presence of ultrasonic waves, resulting in a path similar to that produced by the GRIN lens of View (a).

The method described herein uses the target scattering tissue as the modulated medium in which the light path is controlled, to produce a sculpted virtual lens in the medium. This approach is fundamentally different from traditional acousto-optic, technologies, which require a separate medium. Non-invasive high frequency sound waves, for example, ultrasonic waves, can be used to increase the depth of penetration of light into tissue and shape the propagating beam in a noninvasive manner, while providing real-time reconfigurability of the light wavefront modulation within the tissue itself. The sculpted refractive index contrast, generated by the stationary pressure wave in the medium inside the transducer cavity, results in a gradual focusing of a collimated beam of light, similar to that of a physical GRIN lens, as shown in FIG. 1. View (a) shows the ray path of a collimated beam passing through a Graded-index (GRIN) lens. View (b) shows that, when a collimated beam of light enters a piezo-transducer, its path remains unvaried when the ultrasonic transducer is OFF. View (c) shows the change in the path of the collimated beam when the ultrasonic transducer is activated, resulting in a light path comparable with that of a traditional GRIN lens.

By controlling the intensity of the sound waves, the axial location of the focus can be precisely scanned, thereby changing the numerical aperture of the sculpted virtual lens. The virtual lens can also be scanned along the lateral (radial and azimuthal) direction by using an array of ultrasonic transducers to scan over a surface of the target sample. The combination of axial and lateral scanning provides a 3D volume scanning imaging mechanism.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

DETAILED DESCRIPTION

Interfering ultrasonic waves create a graded refractive index profile within the medium. High frequency sound waves may be created using transducers of varying shapes or transducer arrays. As used herein, the term "transducer" should be interpreted to mean a single transducer or an array of transducer elements. Herein, an exemplary embodiment of the invention is presented in which a cylindrical transducer is used, however, the invention is not meant to be limited thereby. In the exemplary embodiment of the invention, the cylindrical transducer may be of dimensions ID=38 mm, OD=44 mm, h=30 min and may be composed of PZT (lead zirconate titanate ($Pb[Zr(x)Ti(1-x)]O3$)), having internal and external surfaces covered by a conductive epoxy silver layer. Note that these dimensions are exemplary only and are not intended to limit the scope of the invention. Transducers of other dimensions and compositions may be equally acceptable. Because of its geometric properties, pressure standing waves are generated inside the cylindrical cavity at well-defined resonance frequencies, so the radial location of peaks and troughs (antinodes) is fixed in space at each frequency.

Figure 2:
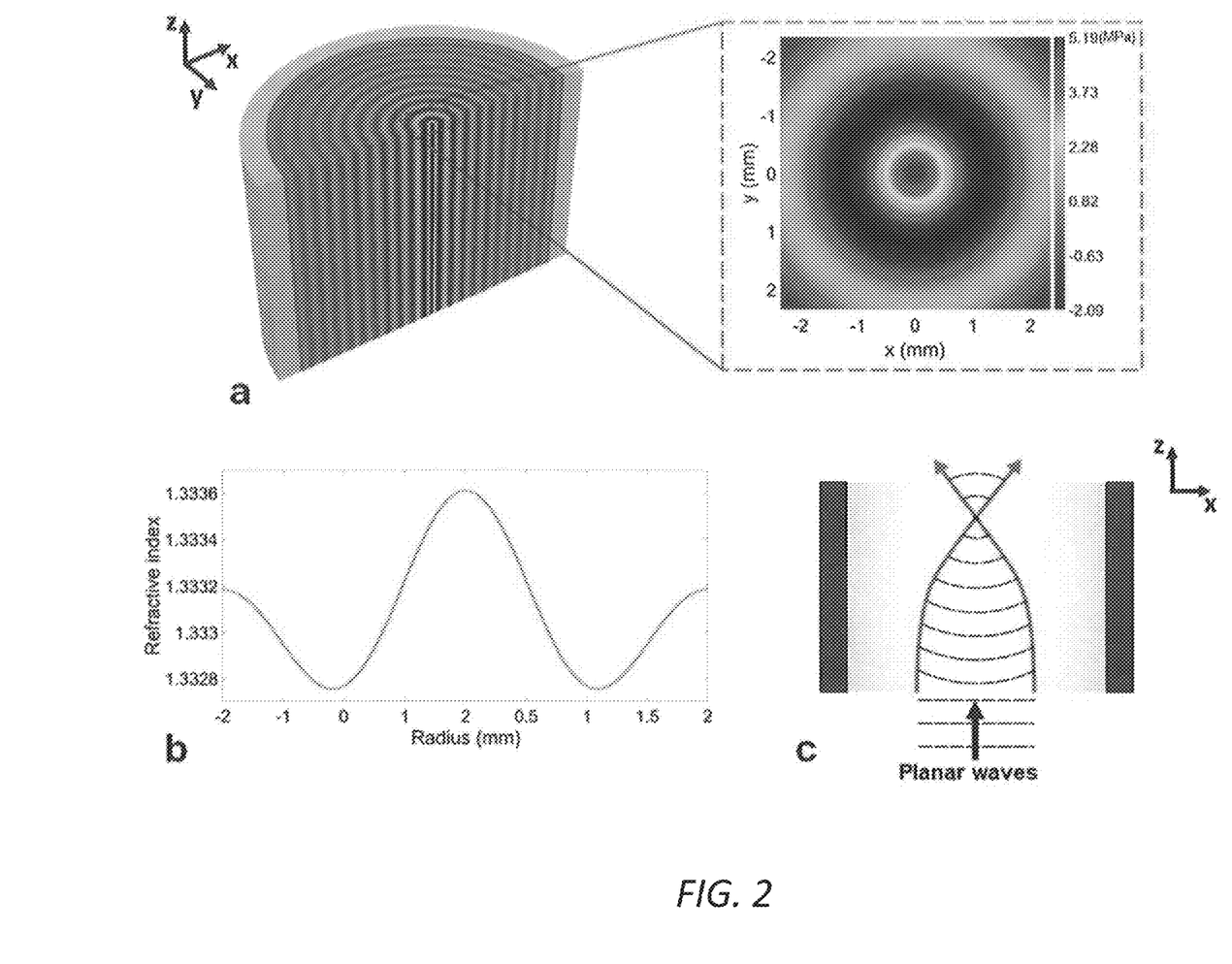
FIG. 2, View (a) schematically shows a radial pressure profile inside the ultrasonic cavity of a cylindrical piezo-transducer, filled with water; the inset shows the detail of the 2D pressure profile at the radial center of the transducer. View (b) shows a cross-section of the refractive index profile inside the transducer when the water is modulated by ultrasonic waves. View (c) shows the ultrasonically sculpted refractive index, contrast tunes the wavefront propagation of the input planar light wave.

View (a) of FIG. 2 shows the pressure field inside the transducer array when it is immersed in water. It is assumed that the pressure profile is constant along the axial direction of the transducer. In simulations, the maximum pressure is $P_{max}$=5.19 MPa when the array is driven by a sinusoidal signal having amplitude $V_0$=34V at the resonance frequency of $f_{res}$=832 kHz. It should be noted that the pressure of the circular region surrounding the central peak, where it reaches its minimum value, is negative. Note that these values are exemplary only and are not intended to limit the scope of the invention. The choice of frequency is a design parameter and depends on several factors, including the properties of the medium, propagation loss, desired wavelength and the characteristics of the electronic drive circuitry. The optimum frequency range can be chosen depending on the application, region of the body or the target medium. As such, many combinations of voltage and frequency may be equally acceptable.

The refractive index of any medium is dependent on its density, which can be directly modulated by ultrasonic waves. The medium is compressed in the high-pressure regions resulting in a higher density, while it is rarefied in the negative pressure areas, where the local density is reduced. As a result, the pressure standing waves create a local refractive index within the medium. For example, the pressure profile inside the cylindrical cavity of the transducer, whose cross-sectional profile is shown in View (b) of FIG. 2, corresponding to a $0^{th}$ order Bessel function. The refractive index profile may be calculated from the simulated pressure profile by the following relation:

$$n(r)=1.333+P(r')*k \qquad (1)$$

where n(r) is the radial refractive index s the radial pressure inside the transducer and $$k = \frac{0.013}{1100}$$

is an empirical factor correlating pressure and refractive index for water.

Multiple lobes in a Bessel profile can be identified, but the highest refractive index contrast is achieved in the central lobe, where $\Delta n=8.5\times10^{-4}$. The geometry of the cavity is symmetrical and, therefore, the pressure will be maximized at the center. The refractive index of the central lobe varies gradually along the x-axis with a quasi-parabolic trend hence the analogy with Graded-Index optics. Similar to a GRIN lens, when a collimated beam of light (planar wavefront) is coupled to the central lobe, its wave phase will be modulated. In particular, the wavefront propagation velocity v will slow down proportionally to the local refractive index value n, according to the relation $$v = \frac{c}{n}.$$

As shown in View (c) of FIG. 2, light will be gradually focused to a focal point having a planar location dependent on the geometry of the array (center for a cylindrical cavity), while the axial location is defined by the wavefront modulation strength, that is, by how much the refractive index affects the wave phase of light.

Figure 4:
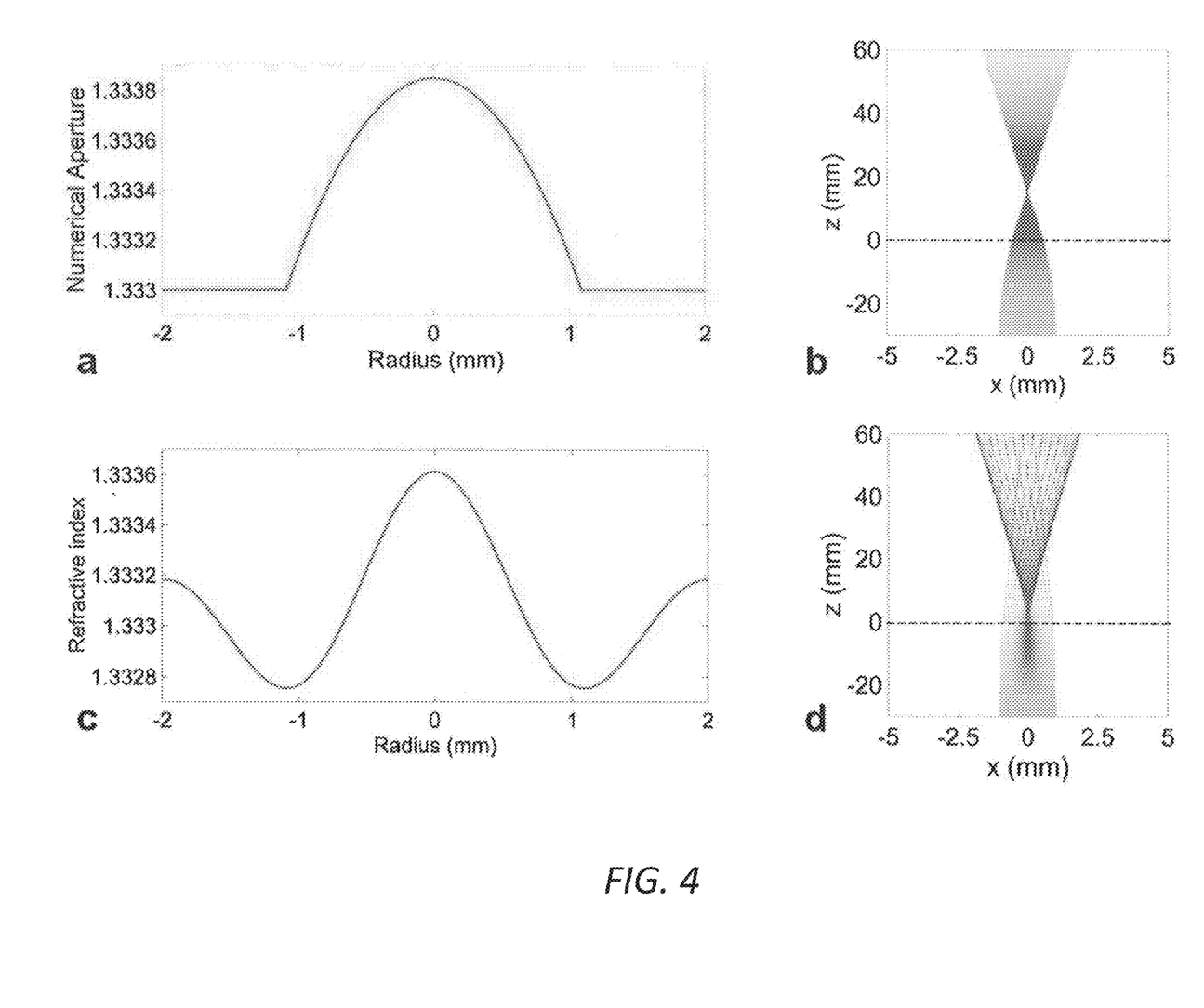

However, differently from a GRIN lens, the shape of the ultrasonically generated lobes is not perfectly parabolic, so not all the light rays will be directed exactly at the same axial focal position, resulting in a long depth of focus (DOF), as shown in Views (b,d) of FIG. 4.

So far, the relations between pressure, refractive index, wavefront modulation and axial location of the focal point have been established. In a piezo-transducer, the generated pressure is a consequence of the wall displacement generated by the electric field, so it is directly proportional to the electric field strength. Therefore, the wavefront modulation can be reconfigured in real-time by varying the refractive index contrast in the medium inside the transducer, which can be achieved by controlling the voltage fed to the array, as shown in View (a) of FIG. 3.

Variations in the refractive index contrast reflect also in the value of the numerical aperture. In a Graded-Index lens, the numerical aperture (NA) is defined as:

$$NA = \sqrt{n_{max}^2 - n_{min}^2} \quad (2)$$

Figure 3:
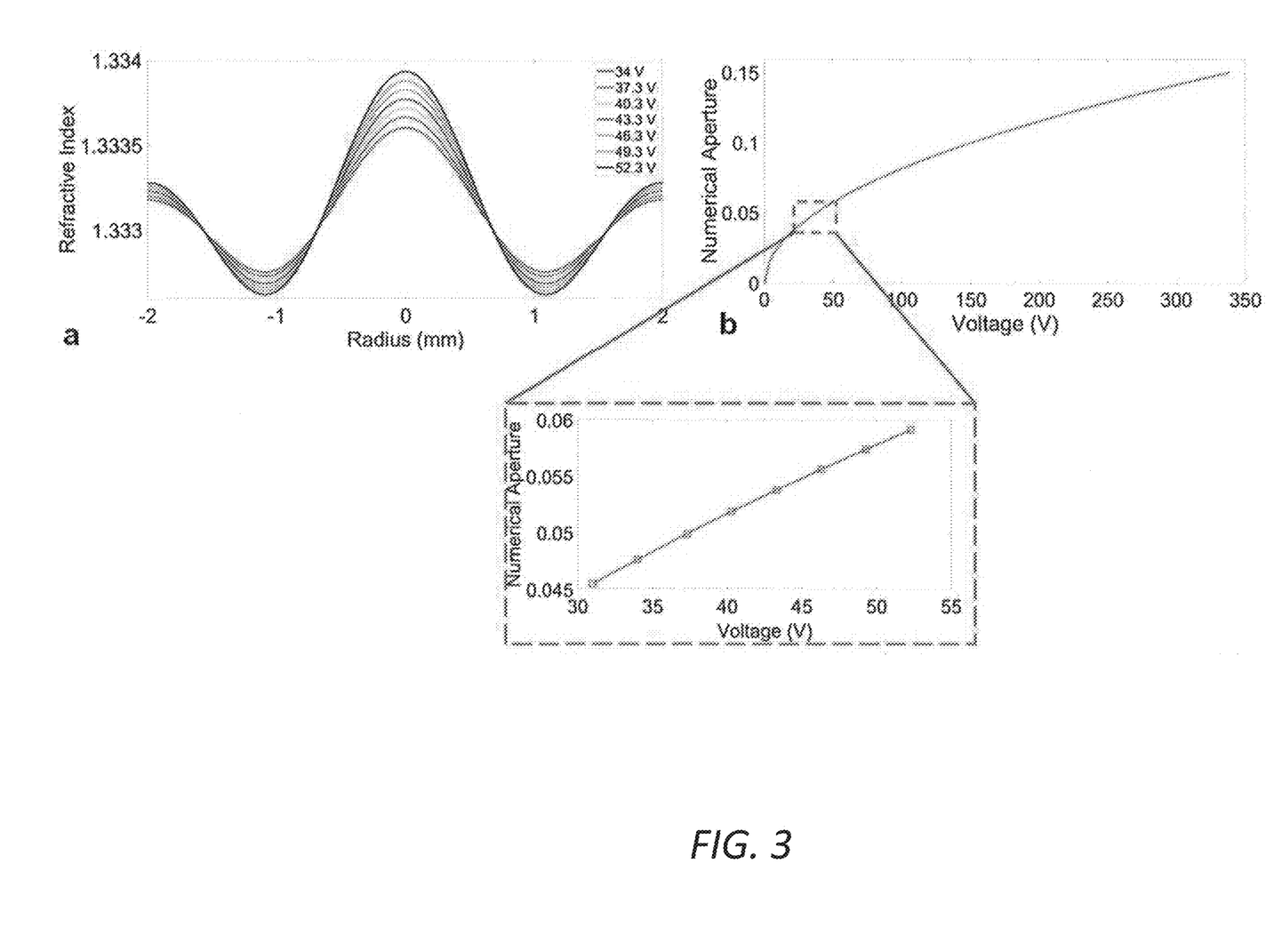
FIG. 3, View (a) shows that the positive and negative peaks of the ultrasonically sculpted refractive index profile change with the voltage. View (b) is a graph showing that increasing the intensity of the ultrasonic waves results in an increase of the NA of the virtual acousto-optic lens. In the inset of View (b), variation of the NA for the voltages used in the experiments is shown, FIG. 4, View (a) shows the parabolic refractive index profile with a maximum contrast. View (b) shows the resulting ray tracing result for a 3 cm long GRIN lens (top edge indicated by dashed black line). View (c) shows the $0^{th}$ order Bessel refractive index profile with a maximum contrast. View (d) shows the resulting ray tracing result for a 3 cm long piezo-transducer (top edge indicated by dashed black line).

Therefore, the higher the refractive contrast, the higher the numerical aperture, as shown by the graph in View (b) of FIG. 3, and the lower the location of the focal point along the z-axis. More powerful virtual lenses can be sculpted in the tissues at higher voltages. For the voltages employed in simulations, ranging from 31V to 52.3V, as shown in the inset of View (b) of FIG. 3, the NA varies from 0.0455 to 0.0591. A voltage increase of 21.3V results in a 30% increase of the NA.

The ultrasonic tagging of light inside the transducer is simulated by ray tracing. The ray path x(z) in a graded structure can be determined by solving the Eikonal equation (Eq. (3)). Because the variation of the refractive index along the x-axis is small, the paraxial approximation can be used. Another condition to simplify the solution of Eq. (3) is that the refractive index is constant along the z-axis, so $$\frac{dn}{dz} = 0.$$

$$\frac{d^2x}{dz^2} = \frac{1}{n(x)} \frac{dn(x)}{dx} \quad (3)$$

While it is possible to analytically solve the Eikonal equation for a traditional parabolic refractive index profile, the solution for a $0^{th}$ order Bessel function is not trivial. To analyze the ray propagation, a custom MATLAB code for numerically solving the Eikonal equation may be used. The initial conditions $x_i$ and $x_i'$, respectively the initial position and slope of the input rays, were set to $x_{i=[-1:1]}$ and $x_i'=0$, to represent a 2 mm wide collimated laser beam. The condition $$\frac{dn}{dz} = 0$$

is valid inside the transducer because of the symmetric and ideally uniform pressure field generated by ultrasound, but it is no longer valid at the interface between the transducer and the medium. In fact, the refractive index of the medium outside the transducer is n=1.333. To keep into account the propagation of the rays in in homogeneous media, Snell's Law may be used for calculating the refraction of the beam at the interface. The pressure profile generated by the standing wave inside the transducer is Obtained via simulations, which is then converted to the refractive index profile according to Eq. (1).

View (a) of FIG. 4 shows the ray paths calculated for a typical GRIN (parabolic) profile, and the $0^{th}$ order Bessel refractive index profile, shown in View (c) of FIG. 4 generated inside the ultrasonic transducer. In both cases the maximum refractive index contrast was set to be $\Delta n=8.5\times 10^{-4}$. The length is assumed to be 3 cm, both for the GRIN lens and the ultrasonic transducer.

Despite the refractive index contrast being the same for both cases, the different profile shapes affect the axial location of the focus. In particular, the focal point is located at z=15.1 mm for the parabolic profile of View (b) of FIG. 4, while it is located at z=0.2 mm for the central lobe of the Bessel function, shown in View (d) of FIG. 4, which is almost at the top edge of the transducer.

The reliability and accuracy of ray tracing has been substantiated by comparing the results of the simulations with experimental results. Using the custom optical characterization setup shown in View (A) of FIG. 5, the profile of a laser beam propagating inside the transducer was imaged. For this characterization, a homogeneous scattering solution made of DI water and $2\times10^{-4}$% Intralipid emulsion was used. This solution meets the minimum requirements for this imaging procedure: transparency to the laser wavelength, homogeneous scattering and very low attenuation of the beam.

To image the beam in the region of interest (i.e. inside the ultrasonic cavity) a lateral window in the cylindrical transducer was opened by cutting off a small region of the wall (approximately a 4 mm arc length). The transducer is placed inside a transparent tank filled with the solution and a 650 nm laser beam is aligned with the radial center of the transducer. Because the antinodes of the pressure standing wave generated by the transducer oscillate over time, the laser was pulsed at the same frequency as the transducer, to make sure that light interacts with the pressure pattern always at the same moment, i.e. when the central peak is at its maximum, as shown in View (d) of FIG. 5. This ensures the best focusing obtainable by this acousto-optic method for a given voltage, other than a reduction of the background light, thus a better imaging contrast.

Figure 5:
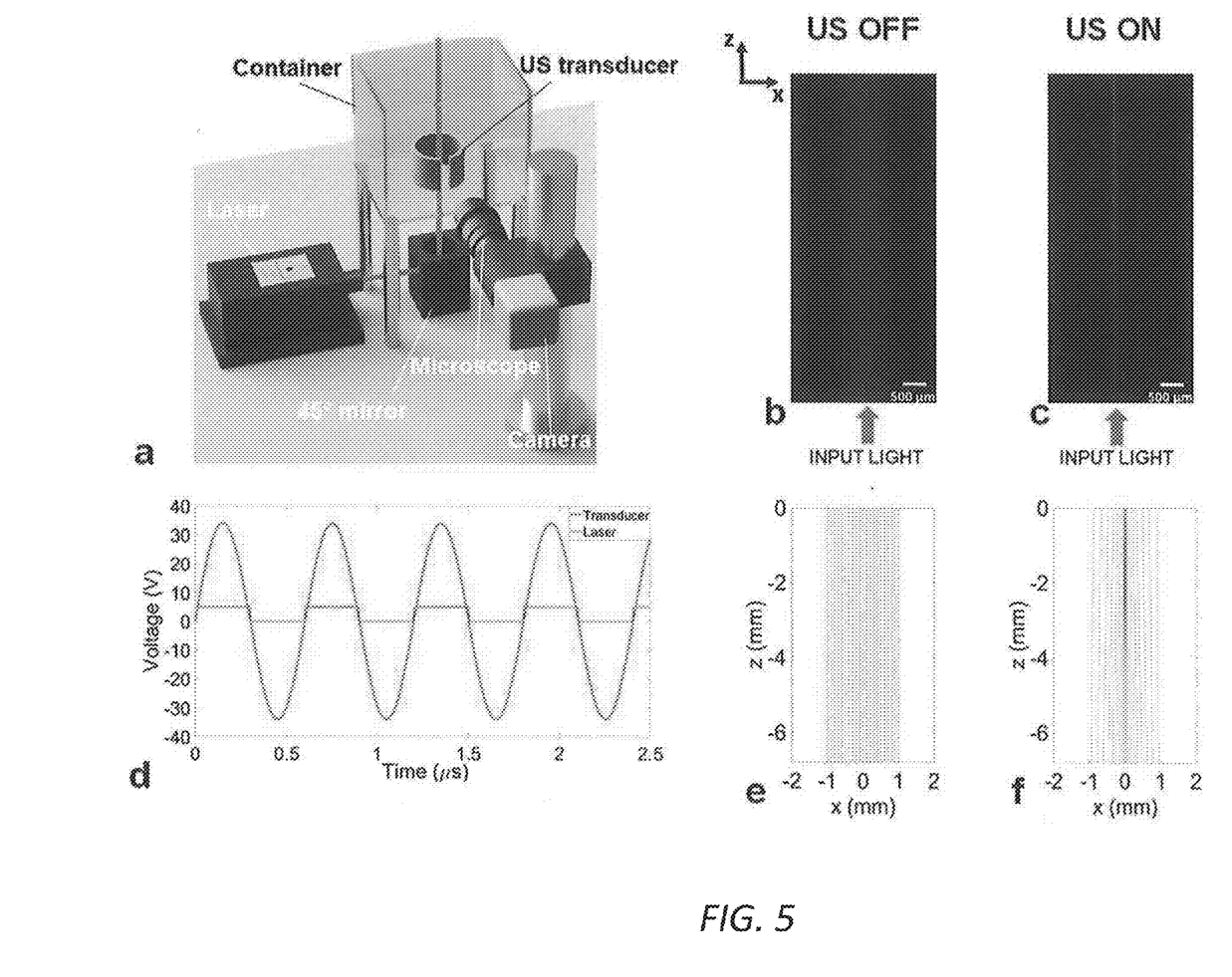
FIG. 5, View (a) is a schematic of the optical characterization setup used to verify the invention. View (b) is an experimental picture of the laser beam when the transducer is OFF and View (c) shows the same view when the transducer is turned ON. View (d) is a graph showing a pulsed laser modulated to match the positive semi-period of the sinusoidal signal feeding the transducer. Views (e-f) shows ray tracing simulations of the laser beam for the same frequency and voltages used for the pictures of Views (b-e), respectively.

When the ultrasonic transducer is OFF, the laser beam remains collimated along its propagation path, as shown in View (b) of FIG. 5. Activating the ultrasound, the refractive index of the water inside the ultrasonic cavity is modulated, generating the beam profile shown in View (c) of FIG. 5. Both cases are properly predicted by the simulations shown in Views (e-f) of FIG. 5, respectively.

Reconfigurable ultrasonic wavefront modulation enables real-time axial scanning of the medium inside the transducer, By controlling the voltage at which the array is driven, the refractive contrast of the medium inside the ultrasonic cavity can be reconfigured in real-time. More precisely, working at a fixed frequency of $f_{res}$=832 kHz, any change to the input electric signal amplitude will be reflected on the piezoceramic displacement in just t=1.2 µS, In the context of bio-applications, this can be considered as "real-time' because most of the biological processes happen in the millisecond range.

When the voltage increases, the values at the antinodes of the stationary pressure wave become larger for the peaks and smaller for the surrounding troughs, as shown in View (a) of FIG. 3, thus the maximum refractive index contrast of the modulated medium increases. In the context of wave propagation, this results in a stronger modulation of the phase front and, as an effect, the wave will converge to the focal point sooner along the z-axis. Therefore, increasing the transducer voltage in a continuous way will result in an axial scanning of the focal point along the negative direction of z-axis.

To establish a quantitative correlation between voltage and axial position of the focus, which can be used to predict the expected location of the axial focus during experiments, nine simulations at $f_{res}$=832 kHz were run, starting from 31V and increasing the voltage by 3V at each iteration. The distance between a reference point (z=0 mm, the top edge of the transducer) and the location of each focal point was measured.

Ultrasound enables increased light penetration and real-time reconfigurability of the beam shape within scattering tissue. The novelty of the invention is that the results described above can be extended to scattering media, such as biological tissue.

Different from other external optics used to shape the beam as it enters the biological tissue, the invention works by using the tissue itself as modulating medium.

Figure 6:
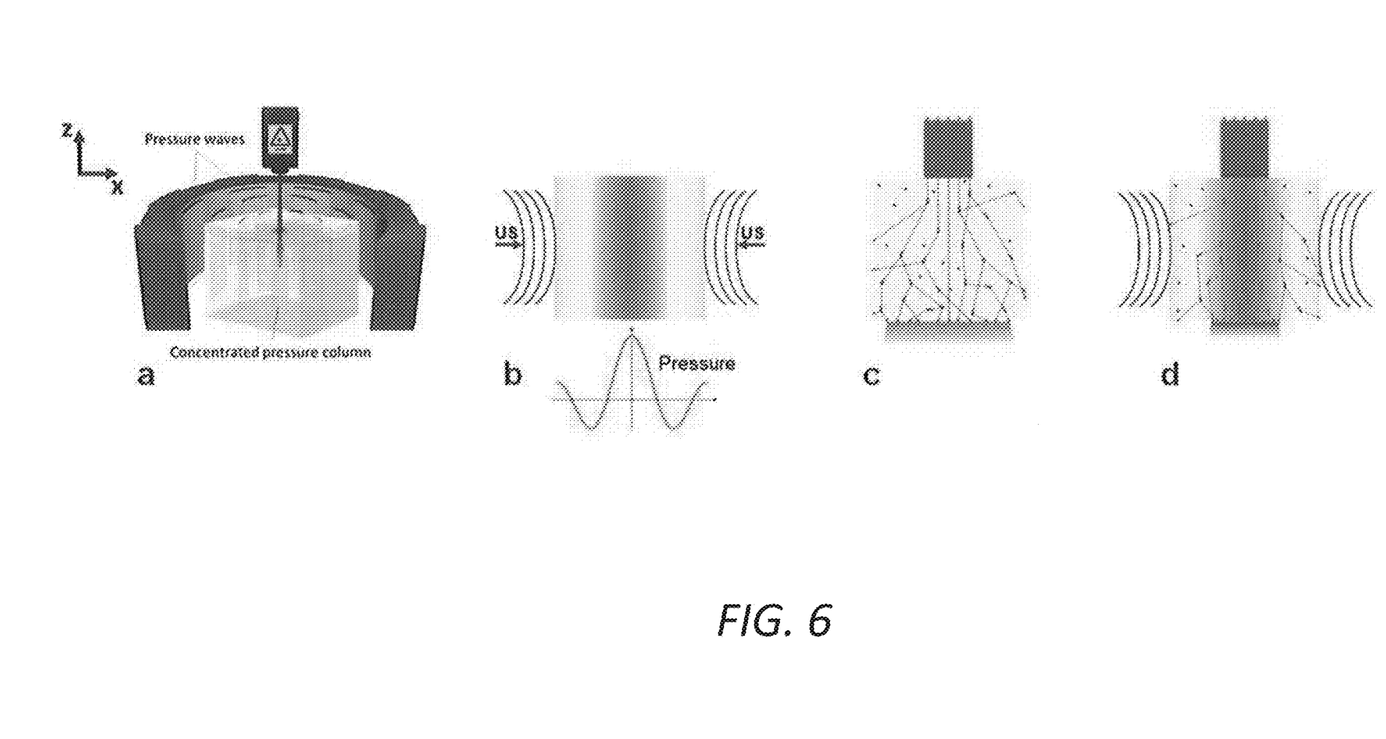
FIG. 6, View (a) is a schematic illustration of ultrasonically sculpted waveguide formation in tissue. View (h) shows a local refractive index contrast generated in the tissue by ultrasonic pressure waves, View (c) shows how a collimated light beam is expanded as result of scattering in the tissue. View (d) shows light being guided in the high refractive index region by the invention, counterbalancing the effect of the scattering.

Ultrasound propagates in biological tissue non-invasively, and with minimum loss (~0.3-0.6 dB/cm·MHz), so the sample can be placed into the transducer with a minimum effect on the ultrasonic pattern inside the cavity, as shown in View (a) of FIG. 6. The standing pressure wave will act on the tissue itself and, similarly to what happens with water, pressure causes changes in density. Thus, in the local refractive index of the biological tissue shown schematically in View (b) of FIG. 6, the ultrasonically sculpted refractive index contrast will now act as a GRIN lens inside the tissue itself.

When a collimated beam enters a biological tissue, the effect of scattering diffuses the photons, shown schematically in View (c) of FIG. 6, such that the output beam will be wider and its intensity lower. However, when the refractive index contrast is ultrasonically sculpted into the tissue, the focusing effect of the virtual lens will compete with scattering, resulting in a narrower and higher intensity output beam, as shown schematically in View (d) of FIG. 6.

Local modulating the local refractive index of the tissue not only increases the depth of penetration of the light beam, but also enables the real-time reconfigurability of the beam shape. In experiments, a scattering phantom tissue made of 2% Agar and 0.1% Intralipid was used to mimic the mechanical and scattering characteristic of scattering biological tissue. The reduced scattering coefficient for the phantom was measured to be $\mu_s'$=1.35 cm$^{-1}$ using Oblique Incidence Reflectometry (OIR).

Figure 7:
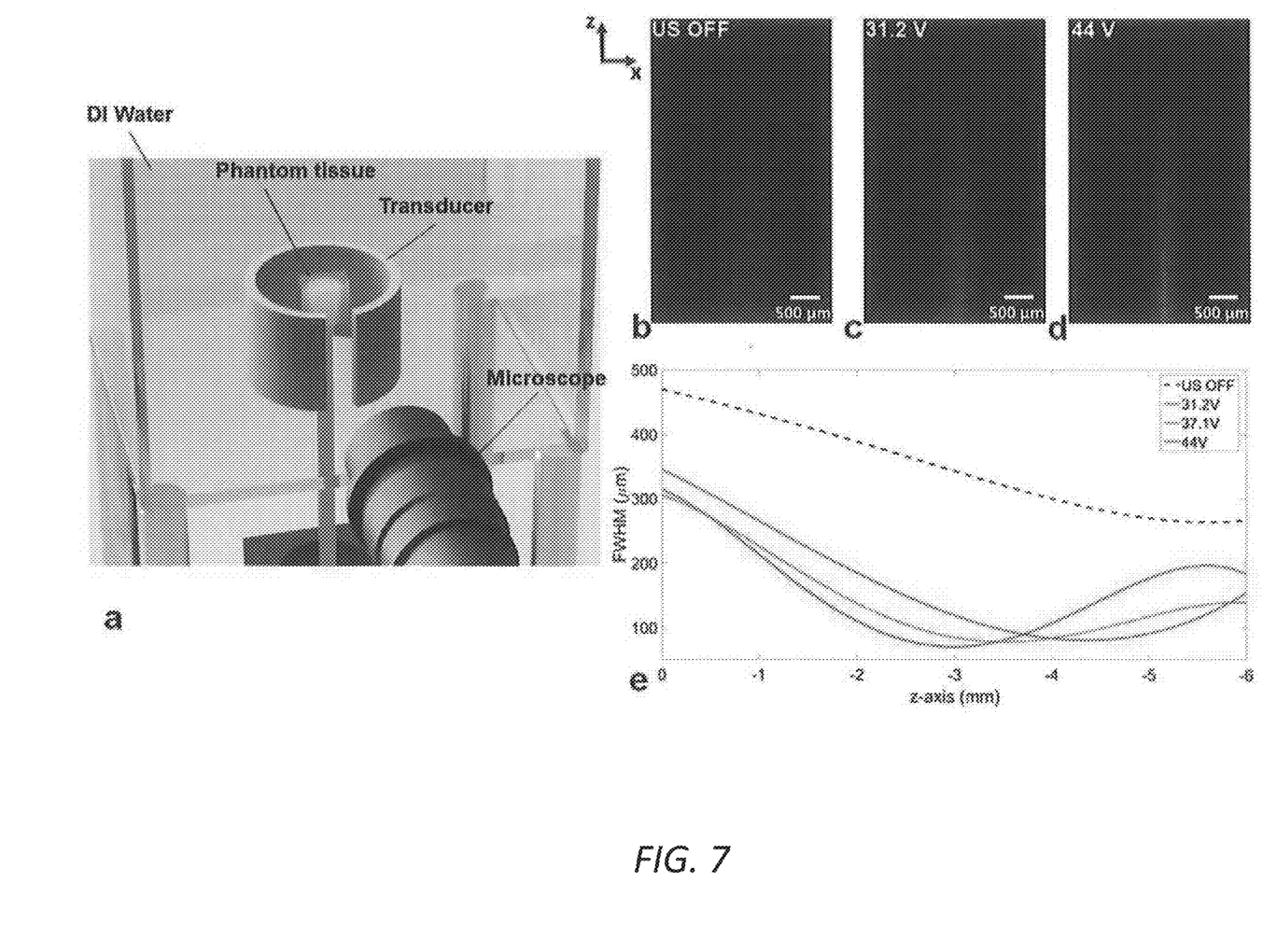
FIG. 7, View (a) is a schematic view of the setup used for laterally imaging the propagation of light inside a scattering tissue phantom. Experimental pictures of the beam of light penetrating the scattering phantom when the transducer is OFF, in View (b) and when the transducer is turned. ON, in Views (c-d), with different voltages. View (e) shows FWHM profiles of the light intensity propagating along the z-axis from the bottom of the sample to the top edge of the transducer.

To test the effect of ultrasound on the tissue phantom, the tissue phantom was placed 6 milt inside the transducer and aligned with the setup, as shown in View (a) of FIG. 7, to make sure that the light beam impinged perpendicularly to the bottom facet of the phantom. The whole beam of light passes through the sample and immediately behind the imaged surface, so that the images taken from a camera are not blurred (typical limitation of imaging in scattering media). When the transducer is OFF, the effect of scattering is evident, expanding the laser beam and reducing the intensity along the propagation direction, shown in View (b) of FIG. 7. When the transducer is activated and fed with 31.2V, ultrasonic waves sculpt a refractive index contrast profile inside the phantom tissue, enabling the focus of the beam through the tissue and contrasting the scattering, shown in View (c) of FIG. 7. The effect of the ultrasound becomes more evident when the voltage is increased to 44V. More light is focused into the tissue, resulting in a higher intensity, and for a longer distance, shown in View (ii) of FIG. 7.

View (e) of FIG. 7, shows a plot of the evolution of the full width at half maximum (FWHM) of the light beam within the sample along the z-axis, to verify and quantify the in-tissue focus axial scanning enabled by ultrasound. When the transducer is OFF, the laser beam can penetrate 0.53 mm into the tissue without widening, Past that point, its FWHM monotonically increases from 264 µm to 470 µm at the top edge of the transducer. When the transducer is turned ON, the initial FWHM of the beam, at z=−6 mm (the bottom of the sample), is between 140 µm and 183 µm, depending on the voltage used. The initial size is lower compared to the laser beam alone because the wavefront of the light starts being modulated by ultrasonic waves as soon as it enters the ultrasonically modulated region (i.e., z=30 mm) so the light beam is already partially focused, After entering the scattering tissue, the light wins the effect of the scattering and continues to be focused. For V=32.1V, the beam continues to be focused until z=−4.36 mm, the axial location of the minimum FWHM, before the effect of the scattering becomes dominant and gradually disperses the light while it propagates. Increasing the voltage results in an increasingly deeper light penetration, as demonstrated from the negative peak of the FWHM for V=37.1V and V=44V, located respectively at z=−3.52 mm and z=−2.98 mm. As shown by simulation in water, photons tend to bend towards the region with the highest refractive index, and the higher the refractive index contrast, the stronger the effect on the photons. This means that photons with a small scattering angle are more likely to be redirected towards the center of the Bessel-shape beam. Therefore, the focusing effect of the sculpted virtual lens will be stronger for higher voltages, because its NA is also increasing.

In accordance with this invention, an ultrasonic wave may be employed to sculpt a virtual, reconfigurable GRIN lens capable of non-invasively modulating and shaping in real-time the wavefront of a laser beam in water and within scattering tissue. The crucial difference with other acousto-optic techniques, such as TAG lenses and AO modulators, is that the presented method operates inside the ultrasonic cavity. Therefore, the transducer no longer acts like an external optics, but actively modulates the properties of the medium, namely its refractive index. The modulation of the wavefront propagation of a planar wave (collimated laser beam) can be quickly changed, with a reconfiguration time in the micro-second range, by varying the amplitude of the sinusoidal input voltage fed to the piezoelectric transducer at the selected frequency (in the exemplary embodiment herein, the selected frequency $f_{res}$=832 kHz). As a direct result, the focal point along the axial direction in the medium (water+2×10⁻⁴% Intralipid) can be scanned by 5.37±0.22 mm inside the transducer by varying the voltage between 34V and 52.3V. The applicability of the invention in-tissue has been demonstrated by scanning the axial focus up to 3 mm inside a 6 mm thick scattering tissue phantom, made of 2% Agar+0.1% Intralipid, when using a voltage range between 31.4V and 44V.

The axial scanning range is strictly dependent on the ultrasonic system parameters, such as dimension of the transducer and maximum voltage supported. Therefore, transducers having a longer length or capable of generating higher pressure into the target medium, enabling the scanning of the focus for lower refractive index contrast (thus at lower voltages), will be able to achieve longer axial scanning ranges. It should be noted that all values used experimentally or as examples herein are not meant to limit the scope of the invention to those values but are provided only to illustrate the invention.

The unique in-tissue feature of the invention may be an enabling factor for innovative, non-invasive imaging and therapeutic applications where light plays a central role, currently limited to shallow depth and fixed location of the focus.

We claim:

1. A method for inducing a virtual lens in a medium comprising:
   directing interfering high-frequency sound waves produced by one or more transducers into the medium to create a plurality of pressure standing waves in the medium, the plurality of pressure standing waves resulting in a local refractive index contrast in a portion of the medium;
   wherein the local refractive index contrast is created by a high-pressure field in the medium created by additive peaks from the interference of the high-frequency sound waves;
   wherein the local refractive index contrast forms the virtual lens in the medium; and
   wherein the virtual lens focuses a collimated beam of light directed into the medium.

2. The method of claim 1 wherein the high-frequency sound waves have a fixed frequency.

3. The method of claim 1 wherein an axial location of a focus of the virtual lens is a function of amplitude of the high-frequency sound waves.

4. The method of claim 2 wherein a numerical aperture of the virtual lens changes with an intensity of the high-frequency sound waves.

5. The method of claim 4 wherein the numerical aperture along a radial center of the one or more transducers is the equation:

$$n(r)=1.333+P(r')*k$$

wherein P(r) is radial pressure and k is an empirical factor correlating pressure and refractive index for the medium.

6. The method of claim 1 wherein the transducer is cylindrical and further wherein the high-frequency sound waves are induced in the medium located inside of the transducer.

7. The method of claim 6 wherein a cross-sectional profile of the local refractive index corresponds to a 0th order Bessel function.

8. The method of claim 7 wherein the 0th order Bessel function has a main lobe and one or more secondary lobes and further wherein pressure in the medium will be maximized at a radial location of the main lobe.

9. The method of claim 8 wherein the local refractive index varies parabolically as a function of a radial location from a center of the main lobe.

10. The method of claim 9 further comprising:
    directing the collimated beam of light into the medium;
    wherein a phase front of the collimated beam of light will be modulated when coupled with the main lobe.

11. The method of claim 1 wherein the collimated light beam is focused to a focal point having an axial location that is a function of strength of the pressure standing waves, wherein the pressure standing wave is an ultrasonic wave.

12. The method of claim 1 wherein the medium is biological tissue.

13. The method of claim 1 wherein the medium is a turbid medium.

14. The method of claim 1 wherein the virtual lens mitigates scattering photons of the collimated beam of light.

15. An apparatus for inducing a sculpted virtual lens in a medium comprising:
    a transducer, for directing interfering high-frequency sound waves into the medium to create pressure standing waves in the medium, the pressure standing waves resulting in a local refractive index contrast in a portion of the medium;
    wherein the local refractive index contrast is created by a high-pressure field in the medium created by additive peaks from the interference of the high-frequency sound waves;
    wherein the local refractive index contrast forms the virtual lens in the medium; and
    wherein the virtual lens focuses a collimated beam of light directed into the medium.

16. The apparatus of claim 15 wherein an axial location of a focus of the virtual lens is a function of amplitude of the high-frequency sound waves.

17. The apparatus of claim 15 wherein a lateral (in plane) location of a focus of the virtual lens is a function of an interference pattern created by the high-frequency sound waves.

18. The apparatus of claim 17 wherein the lateral (in plane) location of a focus of the virtual lens can be reconfigured by changing the interference pattern.

19. The apparatus of claim 15 wherein the transducer is cylindrical and further wherein the pressure standing waves are induced in the medium located inside of the transducer.

20. The apparatus of claim 15 wherein the local refractive index contrast changes in three dimensions.

21. The apparatus of claim 15 wherein:
    a cross-sectional profile of the local refractive index contrast corresponds to a 0th order Bessel function having a main lobe and one or more secondary lobes;
    pressure in the medium will be maximized at a radial location of the main lobe; and
    the local refractive index contrast varies parabolically as a function of the radial location from a center of the main lobe.

22. The apparatus of claim 15 further comprising:
    a light source for directing the collimated beam of light into the medium.

23. The apparatus of claim 22 wherein a wave phase of the light beam will be modulated when propagating through the medium with a modulation of the local refractive index contrast.

24. The method of claim 10 further comprising collecting photons from the medium scattered by diffusion within the medium.

* * * * *